United States Patent [19]

Calabria

[11] Patent Number: 5,284,473
[45] Date of Patent: Feb. 8, 1994

[54] PERFUSION CATHETER WITH FLOW AMPLIFIER

[75] Inventor: Mark A. Calabria, Plymouth, Minn.

[73] Assignee: C. R. Bard, Inc., Murray Hill, N.J.

[21] Appl. No.: 730,644

[22] Filed: Jul. 16, 1991

[51] Int. Cl.$^5$ ............................................. A01M 29/02
[52] U.S. Cl. ..................................... 604/53; 604/102; 606/192
[58] Field of Search ........................ 604/8–10, 604/39, 43–45, 51–56, 93, 96, 102, 118, 131, 149, 150, 246, 264, 266, 269, 280; 128/204.24, 204.25

[56] References Cited

U.S. PATENT DOCUMENTS

| | | | |
|---|---|---|---|
| 3,421,510 | 1/1969 | Kettenbach | 604/45 |
| 3,542,031 | 11/1970 | Taylor | 604/269 X |
| 3,628,532 | 12/1971 | Magrath | 604/149 X |
| 4,046,492 | 9/1977 | Inglis | 417/197 |
| 4,195,780 | 4/1980 | Inglis | 239/73 |
| 4,265,237 | 5/1981 | Schwanbom et al. | 128/204.24 |
| 4,305,339 | 12/1981 | Inglis | 112/281 |
| 4,385,728 | 5/1983 | Inglis et al. | 239/424 |
| 4,493,696 | 1/1985 | Uldall | 604/43 |
| 4,555,059 | 11/1985 | Collins et al. | 239/425 |
| 4,581,017 | 4/1986 | Sahota | 604/101 |
| 4,735,606 | 4/1988 | Davison | 604/28 |
| 4,753,221 | 6/1988 | Kensey et al. | |
| 4,755,175 | 7/1988 | Nilsson | 604/268 |
| 4,857,046 | 8/1989 | Stevens et al. | 604/22 |
| 4,857,054 | 8/1989 | Helfer | 604/102 |
| 4,881,542 | 11/1989 | Schmidt et al. | 128/207.14 |
| 4,930,705 | 6/1990 | Broorman | 239/590 |

OTHER PUBLICATIONS

*Van Nostrand's Scientific Encyclopedia*, Sixth Ed., Van Nostrand Reinhold Company, Inc., 1983, pp. 1233–1234.
*Introduction to Fluid Mechanics*, Third Ed., John Wiley and Sons, 1985, pp. 175–176.

Primary Examiner—John D. Yasko
Assistant Examiner—Adam J. Cermak
Attorney, Agent, or Firm—Wolf, Greenfield & Sacks

[57] ABSTRACT

A perfusion catheter is provided which increases the static pressure gradient across a portion of the catheter so that the flow through the catheter having the flow amplifier is greater than the flow through an unamplified catheter. A low pressure region is created at or downstream of the perfusion ports so that a greater volume of blood is drawn in and subsequently discharged through the distal end of the catheter.

4 Claims, 5 Drawing Sheets

PERFUSION CATHETER WITH FLOW AMPLIFIER

FIELD OF THE INVENTION

The invention relates to catheters used in cardiovascular diagnostic and therapeutic procedures such as angioplasty, atherectomy and the like.

BACKGROUND OF THE INVENTION

Among the medical procedures performed by cardiologists is the angioqraphic examination of a patient's coronary arteries and treatment of those arteries by angioplasty to dilate or remove obstructions (stenoses). The coronary arteries, which branch off the aorta, carry oxygenated blood back to the heart muscle itself to nourish and sustain the heart muscle (myocardium). After the shape and anatomy of the coronary arteries, and the presence and nature of the stenosis has been determined, a special angioplasty catheter, such as a balloon dilatation catheter or other type of angioplasty catheter is advanced to the site of the stenosis to dilate or otherwise treat the stenosis.

A coronary angioplasty procedure involves the use of several catheters, guidewires and related devices. Initially, a guiding catheter is inserted percutaneously into the patient's arterial system, usually by a percutaneous puncture made in the femoral artery in the groin. A guide catheter is advanced, with the aid of a guidewire, upwardly through the patient's aorta to the region of the heart. The distal end (end inside of the patient) of the guide catheter is specially formed so that when it is disposed in the region of the heart, it will assume a shape that facilitates placement of the distal outlet tip of the catheter at the entrance to (the ostium) one of the two main coronary arteries. Typically, the distal tip of the guiding catheter will enter the ostium very slightly so as to be securely positioned. Once the guiding catheter has been positioned, it provides a direct path for subsequent balloon dilatation or other angioplasty catheters that are intended to enter into the coronary arteries to treat the stenosis.

One problem encountered in the use of balloon angioplasty catheters is the obstruction of blood flow from the proximal side of a stenosis to the distal side while the balloon is inflated. Complete occlusion of a coronary artery usually cannot be tolerated for more than about 30 to 60 seconds without incurring serious risk of damage to portions of the heart which receive blood from the occluded artery. As a result, the balloon may be inflated for only short intervals before it must be deflated to permit the resumption of blood flow. It is preferred, however, to dilate a stenosis with the single relatively long continuous balloon inflation as that technique is thought to reduce the risk of restenosis. A number of proposals have been made to increase the time of balloon inflation. One such solution is described in U.S. Pat. No. 4,581,071 (Sahota) which discloses a balloon dilatation catheter having a blood entry port located on the proximal side of the balloon. The port communicates with the main guidewire lumen of the catheter and enables blood to flow from the proximal to the distal side of the balloon even when the balloon is inflated.

The blood flow rate through such a perfusion catheter is determined by the diameter of the flow lumen within the catheter and the pressure difference across the inlet and outlet ports. Typically, a perfusion catheter permits flow, although at a reduced rate. It would be desirable to provide, in such catheters, increased flow rates approaching that when a catheter is not present.

Pumps have been proposed in connection with perfusion catheters to increase the blood flow downstream of the stenosis. Most of the pumping devices are located externally of the patient and withdraw blood from an upstream location, and then return the blood so that it is expelled downstream from the intake openings. For example, U.S. Pat. No. 4,857,054 (Helfer) discloses a perfusion angioplasty catheter with a pump assist in which one-way valves are employed at intake and ejection apertures so that upstream apertures only draw fluid into the catheter while the downstream apertures only permit the ejection of fluid from the catheter. An external pump is employed to eject and draw in blood without having to withdraw the blood from the patient. The blood flow in the Helfer catheter is pulsatile, not continuous, due to the valving arrangement and piston-type pump employed.

Such pump assisted perfusion catheters tend to be complicated, thus increasing the risk of failure.

There is a need, therefore, for a perfusion catheter which increases the flow of blood through the catheter and which is of relatively simple design. Furthermore, in the event of failure, it is desirable that some blood flow through the perfusion catheter be maintained. It is among the general objects of the invention to provide such a perfusion catheter.

SUMMARY OF THE INVENTION

The invention is incorporated into a perfusion catheter which increases the static pressure gradient across the inlet port portion of the catheter thereby to amplify the flow into and through the central lumen of the catheter. To that end, a low pressure region is created downstream of the perfusion inlet holes so that a greater volume of blood is drawn into the central lumen of the catheter and subsequently is discharged through the distal end of the catheter.

In one embodiment, a separate perfusion assist tube is inserted through the central lumen of the perfusion catheter so that the distal end of the assist lumen is positioned distal the perfusion inlet ports. Saline, blood, or a liquid component of blood is expelled out the distal end of the assist tube at a high velocity. The high velocity jet increases the velocity of the blood in the central lumen of the catheter thereby lowering the static pressure in that region of the central lumen. That, in turn, results in an increased pressure gradient between the inlet port and the region of the high velocity jet. Consequently, the blood flow into and through the catheter is increased. In a second embodiment, the distal outlet end of the perfusion assist tube is connected to a flow amplifier located in the central lumen. The flow amplifier has a Coanda profile to create a high velocity stream of fluid and create the low pressure region downstream of the inlet port. In a third embodiment of the invention, a venturi or narrowing of the inner diameter of the central lumen is located about the inlet port. Consequently, flow through the central lumen is subjected to a pressure drop causing a greater volume of blood to be drawn in through the inlet ports and perfused out the distal end of the central lumen.

It is among the general objects of the invention to provide an improved perfusion catheter with flow amplifier.

Another object of the invention is to provide a perfusion catheter for use in coronary angioplasty and other cardiovascular interventional procedures that allows the perfusion of blood through the catheter, and minimizes the risk of flow amplifier failure.

Another object of the invention is to provide a perfusion catheter having a flow amplifier in which a low pressure region is produced to increase the static pressure gradient across the inlet port thereby increasing the volume of blood drawn in through the inlet ports and expelled out the distal end of the catheter.

A further object of the invention is to provide a perfusion catheter having a flow amplifier which employs a minimum of parts and is therefore less likely to malfunction.

Still another object of the invention is to provide a perfusion catheter having a flow amplifier where unamplified blood flow is maintained in the event of amplifier failure.

DESCRIPTION OF THE DRAWINGS

The foregoing and other objects and advantages of the invention will be appreciated more fully from the following further description thereof, with reference to the accompanying drawings wherein.

DESCRIPTION OF THE ILLUSTRATIVE EMBODIMENTS

Figure 1:
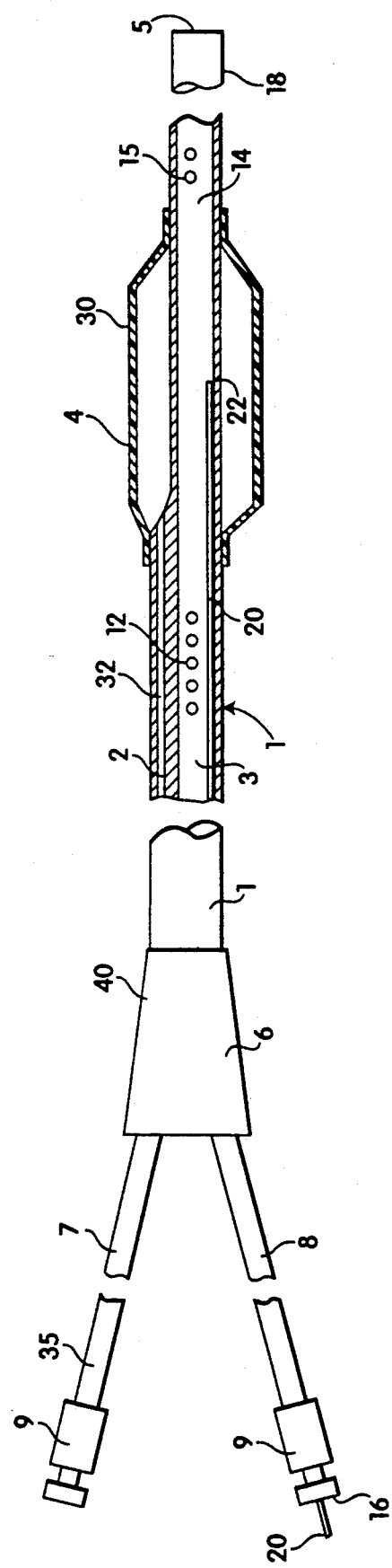
FIG. 1 is an enlarged, fragmented, partial cross-sectional diagrammatic illustration of a balloon perfusion catheter with flow amplifier according to a first embodiment of the invention.

FIG. 1 illustrates, diagrammatically, a balloon dilatation catheter that incorporates a first embodiment of the invention. The catheter includes an elongate flexible shaft having two lumens, including an inflation/deflation lumen and a central guidewire lumen. A balloon is attached to the distal end of the catheter and is in communication with the inflation/deflation lumen 2. The distal end of the central guidewire lumen 3 terminates at an outlet orifice 5 at the distal tip of the catheter. The catheter shaft may be formed from any of a variety of polymeric materials known to those familiar with the art. The balloon may be formed from polyethylene terephthalate or the like in a process as described in U.S. Pat. 4,490,421 to which reference is made and which is incorporated by reference in its entirety. The proximal end of the catheter includes a bifurcate molded fitting 6 and a pair of tubular legs 7, 8. Tublar leg 7 has a luer fitting 9 at its proximal end as does the proximal end of tubular leg 8. Tubular leg 7 communicates with the inflation lumen 2 and tubular leg 8 communicates with the central guidewire lumen 3.

In accordance with the invention, the catheter shaft is provided with a number of proximal perfusion inlet ports 12, connecting the outside of the catheter and the central lumen 3. The foregoing construction is typical of that described in the aforementioned Sahota patent. When the catheter is placed in the patient's coronary vessels, blood will flow from a proximal portion of the coronary artery through the inlet ports 12, central lumen 3 and out of the distal end of the catheter thereby to continually perfuse the portion of the heart served by the distal coronary artery, even while the balloon is inflated. In accordance with the invention, and in order to increase the rate of blood flow through the catheter, a small separate perfusion assist tube 20 is inserted through the fitting 10 and into the central lumen 3 so that the distal end 22 of the assist tube 20 is positioned distally of the perfusion inlet ports 12. Liquid, such as blood, saline or a blood substitute or a component of blood is caused to flow through the assist tube 20 at a relatively high velocity to create a region of low static pressure downstream of the ports 12 thus increasing the static pressure gradient across inlet ports 12. As a consequence, blood is drawn through the perfusion inlet ports 12 at a greater flow rate and is discharged through the distal end 18 of the central lumen 14. Distal side ports 15 may be provided in the tubular shaft of the catheter to facilitate distal blood flow. The perfusion assist lumen 20 may be freely movable within the central lumen 14 of the catheter, or, alternatively, may be attached to the central lumen to fix the location of the distal end 22 thereof.

Figure 2:
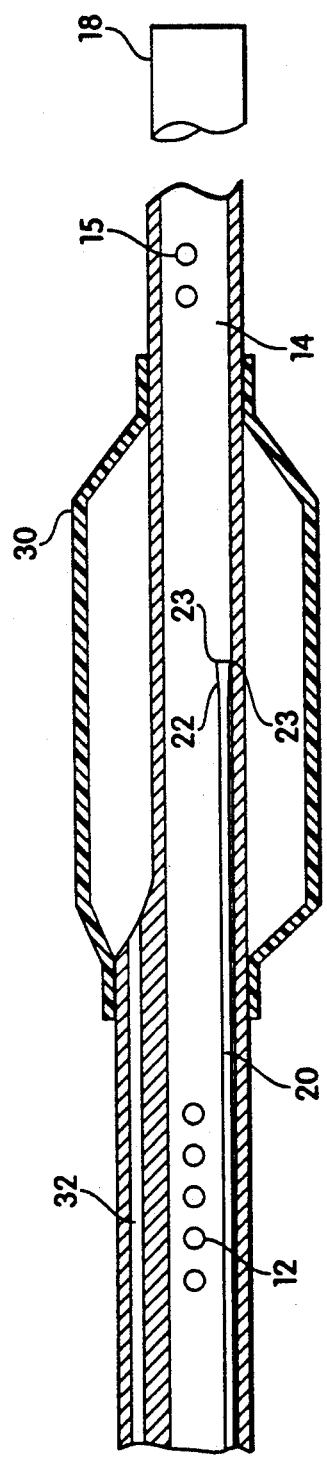
FIG. 2 is an enlarged, fragmented, cross-sectional diagrammatic illustration of a perfusion catheter with flow amplifier illustrated in FIG. 1, in which the distal end of the flow assist lumen is flared.

As shown in FIG. 2, the distal end 22 of the perfusion assist tube 20 may be slightly outwardly flared as indicated at 23. Such flaring reduces the viscous shear stresses when the fluid flows out of the assist tube 20.

If fluid ceased flowing through the assist tube 20 or if the amplifier failed in the first or second embodiments, blood still will perfuse through inlet ports 12. The rate at which each perfusion occurs would be substantially equal to the perfusion rate absent the flow amplifier. Thus, failure of the flow amplifier of the invention reduces the risk of occluding the downstream blood flow, and the possibility of resulting trauma or injury to the patient is less than known pump-assisted perfusion catheters.

Figure 3:
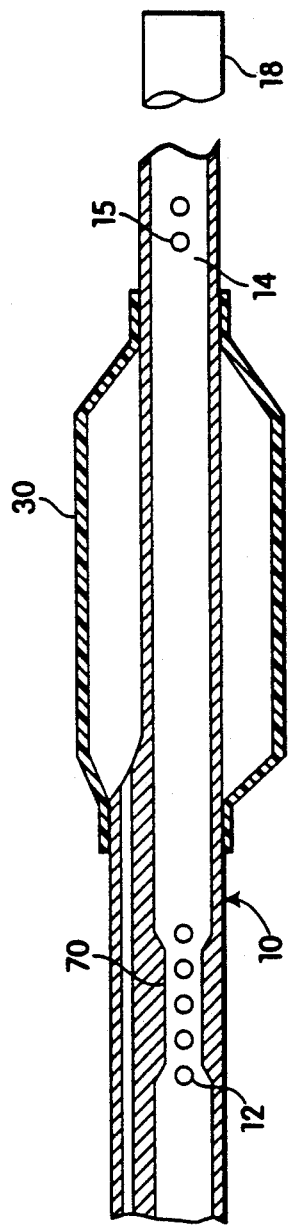
FIG. 3 is an enlarged, fragmented, cross-sectional view diagrammatic illustration of a second embodiment of the invention in which a venturi is provided at the inlet ports of the proximal side of the balloon.

FIG. 3 illustrates another embodiment of the invention in which a venturi, or narrowing 70 of the inner diameter of the central lumen 14 is centrally located about the inlet ports 12. Flow is introduced into the central lumen 14, and due to the venturi 70, a low pressure region is created causing a greater volume of blood to be drawn in through the inlet ports 12 to be perfused out the outlet ports 15 and distal end 18 of the central lumen 14.

To manufacture a perfusion catheter according to the second embodiment illustrated in FIG. 3, the venturi or narrowing 70 of the inner diameter of the central lumen 14 is formed by adding material, such as a slightly smaller diameter ring and attaching it to the central lumen 14 at the proper location. The perfusion inlet holes 12 are subsequently formed through the catheter shaft and the added material. In this manner, blockage of the perfusion inlet holes 12 by the added material is prevented.

Figure 4:
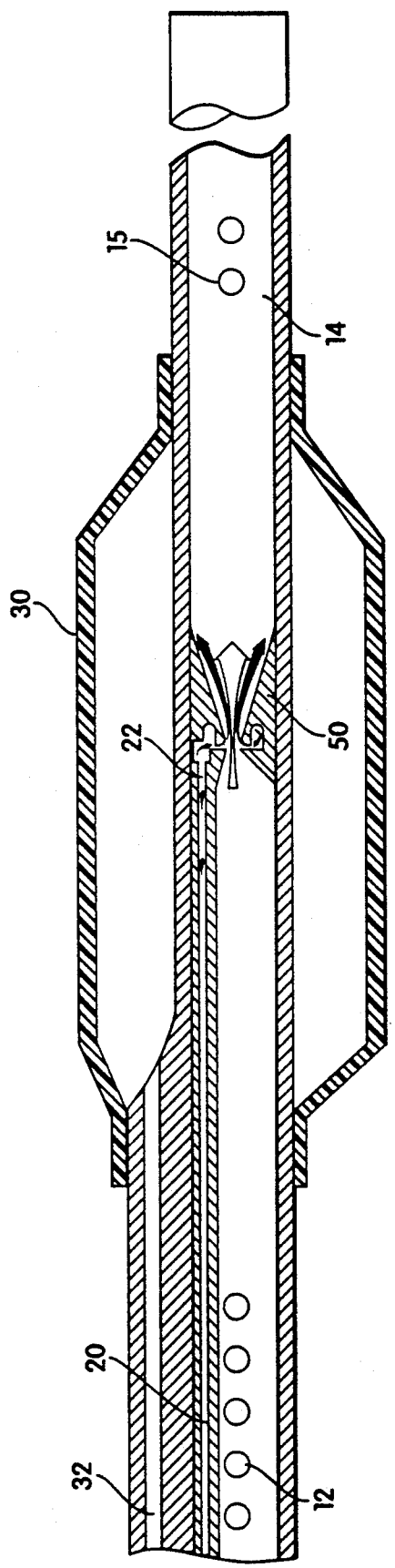
FIG. 4 is an enlarged, fragmented, cross-sectional diagrammatic illustration of a third embodiment of the invention in which the flow amplifier has a Coanda profile.
Figure 5:
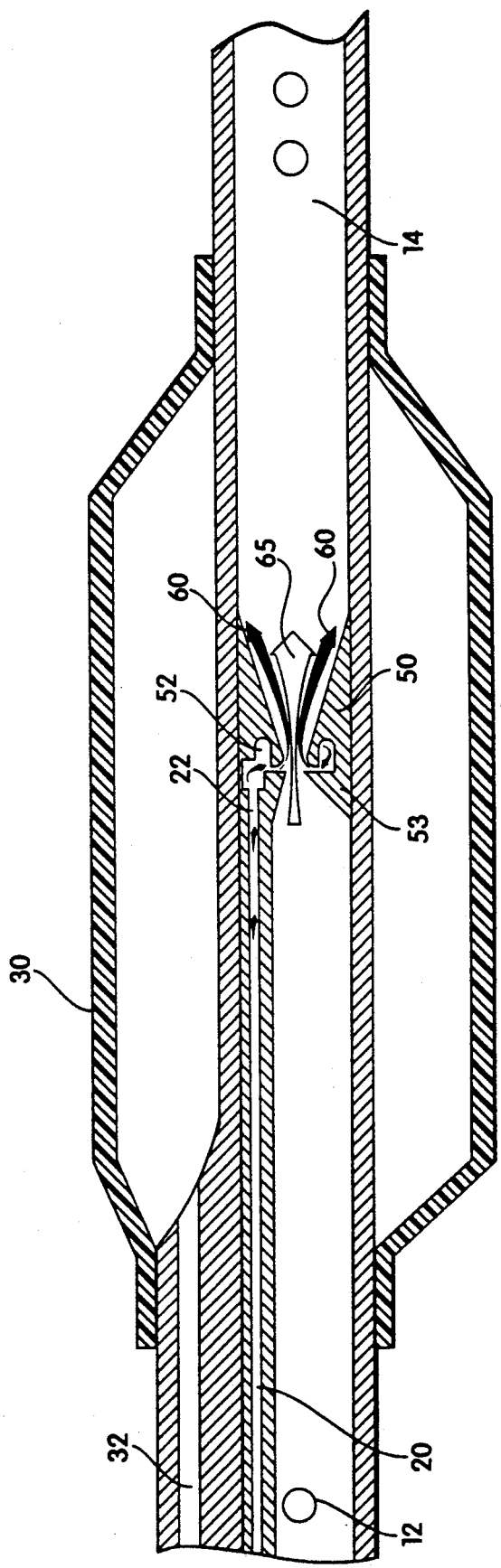
FIG. 5 is an enlarged diagrammatical illustration of the Coanda profile illustrated in FIG. 4.

FIGS. 4 and 5 illustrate a third embodiment of the invention in which a perfusion assist tube 20 extends distally of the perfusion inlet holes 12. The distal end of the assist tube 22 is connected to a fluid flow amplifier 50, which directs a high velocity stream of fluid over a Coanda profile to create a low pressure region at the distal end of the device. As was the case with the first embodiment, blood flows in through the perfusion inlet holes 12 to fill the low pressure region at a faster rate than the case where no flow amplifier is provided.

FIG. 5 shows the Coanda profile in greater detail. Compressed fluid flows from the distal end 22 of the assist lumen 20 into an annular chamber 52. Fluid then is throttled through a small ring nozzle 53 at high velocity, as shown by arrows 60. A low pressure area is created at the center of the amplifier 50 to induce a high volume flow of surrounding fluid into the primary fluid stream 65. The combined flow of the primary 65 and surrounding fluid 60 is exhausted in a high volume, high velocity flow.

All of the embodiments increase the static pressure gradient across a portion of the catheter, so that the flow through the catheter with the flow amplifier is greater than the flow through an unamplified catheter. All of the embodiments have a relatively simple construction, are easy to use, and pose no threat to a patient in the event of failure of the flow amplifier.

From the foregoing, it will be appreciated that I have provided an improved perfusion catheter structure that may be used with coronary angioplasty and other catheters. The amplifier permits continuous blood flow as opposed to pulsatile flow. It should be understood, however, that the foregoing description of the invention is intended merely to be illustrative thereof and that other embodiments, modifications and equivalents may be apparent to those skilled in the art without departing from its spirit.

Having thus described the invention, what I have desired to claim and secure by Letters Patent is:

1. A cardiovascular catheter comprising:
   an elongate flexible tubular shaft having a proximal end, a distal end and a main lumen extending from the proximal end to an outlet orifice at the distal end of the shaft;
   at least one side inlet port formed in a wall of the tubular shaft at a location proximally of the distal end, the side port being in communication with the main lumen, and
   means for developing a low-pressure region in the main lumen distally of said at least one side inlet port to amplify the rate of fluid flow drawn into said inlet port and through the main lumen of the catheter;
   said means for inducing a low pressure region comprising an elongate flexible tube having a proximal end and a distal end, the proximal end of said tube extending proximally of said catheter shaft, and the distal end of said tube is located between the outlet orifice of the catheter and distally of the side port; and
   a balloon located on the distal end of the shaft distally from said at least one side port.

2. A cardiovascular catheter comprising:
   an elongate flexible tubular shaft having a proximal end, a distal end and a main lumen extending from the proximal end to an outlet orifice at the distal end of the shaft;
   at least one side inlet port formed in a wall of the tubular shaft at a location proximally of the distal end, the side port being in communication with the main lumen, and
   means for developing a low-pressure region in the main lumen distally of said at least one side inlet port to amplify the rate of fluid flow drawn into said inlet port and through the main lumen of the catheter;
   said means for inducing a low pressure region comprising an elongate flexible tube having a proximal end and a distal end, the proximal end of said tube extending proximally of said catheter shaft, and the distal end of said tube is located between the outlet orifice of the catheter and distally of the side port;

3. A cardiovascular catheter comprising:
   an elongate flexible tubular shaft having a proximal end, a distal end and a main lumen extending from the proximal end to an outlet orifice at the distal end of the shaft;
   at least one side inlet port formed in a wall of the tubular shaft at a location proximally of the distal end, the side port being in communication with the main lumen, and
   means for developing a low-pressure region in the main lumen distally of said at least one side inlet port to amplify the rate of fluid flow drawn into said inlet port and through the main lumen of the catheter; and
   a balloon located on said shaft near the distal end of said shaft, wherein a proximal end of said balloon is located distally from said at least one side port.

4. A method for increasing the rate of perfusion of blood from a blood vessel through a catheter disposed in the blood vessel to a location in the blood vessel downstream of the catheter comprising:
   providing a catheter having side ports formed in the wall of the catheter thereby to communicate the inner lumen of the catheter with blood in the blood vessel through the side ports;
   introducing a stream of a second liquid into the lumen of the catheter in a manner as to increase the velocity of fluid flow within the lumen of the catheter thereby lowering the static pressure within that region of the catheter thereby to draw fluid into the catheter through the side ports at an increased rate of flow.

* * * * *